(12) United States Patent
Smith et al.

(10) Patent No.: US 10,758,649 B2
(45) Date of Patent: Sep. 1, 2020

(54) HIGH FLOW MANIFOLD

(71) Applicant: Zimmer, Inc., Warsaw, IN (US)

(72) Inventors: Larry C. Smith, Shawnee, KS (US); David J Boles, Copley, OH (US)

(73) Assignee: Zimmer, Inc., Warsaw, IN (US)

( * ) Notice: Subject to any disclaimer, the term of this patent is extended or adjusted under 35 U.S.C. 154(b) by 478 days.

(21) Appl. No.: 15/467,307

(22) Filed: Mar. 23, 2017

(65) Prior Publication Data
US 2018/0272051 A1    Sep. 27, 2018

(51) Int. Cl.
*A61M 1/00* (2006.01)
*B01D 46/00* (2006.01)
(Continued)

(52) U.S. Cl.
CPC ........ *A61M 1/0052* (2014.02); *A61M 1/0001* (2013.01); *B01D 46/0005* (2013.01);
(Continued)

(58) Field of Classification Search
CPC ........ A61M 1/0001; A61M 2205/7536; A61M 1/0052; A61M 2207/00; B01D 46/0005;
(Continued)

(56) References Cited

U.S. PATENT DOCUMENTS

| | | |
|---|---|---|
| 2,275,472 A | 3/1942 | Samiran |
| 4,089,470 A | 5/1978 | Strahman |

(Continued)

FOREIGN PATENT DOCUMENTS

| | | |
|---|---|---|
| CA | 2708597 | 9/2003 |
| CA | 2640549 | 12/2016 |

(Continued)

OTHER PUBLICATIONS

"U.S. Appl. No. 15/496,392, Response filed Aug. 2, 2018 to Non Final Office Action dated Jul. 12, 2018", 8 pgs.
(Continued)

*Primary Examiner* — Krishnan S Menon
*Assistant Examiner* — Waqaas Ali
(74) *Attorney, Agent, or Firm* — Schwegman Lundberg & Woessner, P.A.

(57) ABSTRACT

Implementations described herein include a system for guiding medical waste fluid into a medical waste collection canister. The system includes a manifold and a filter. The manifold includes a top surface and a sidewall extending from the top surface in a first direction. The top surface and the sidewall define an interior chamber of the manifold. The top surface includes an inlet port and a vacuum port disposed therein. The inlet port connects to a source of medical waste fluid and the vacuum port connects to a vacuum source. The manifold can be formed from a first polymer. A filter is positioned within the interior chamber of the manifold and immediately upstream of the vacuum port so as to filter air flowing into the vacuum port. The filter extends away from the top surface of the manifold in the first direction and the filter is formed from a second polymer. The filter is fused to a surface of the interior chamber of the manifold or to a peripheral surface of the vacuum port so as to form a fused interface, and not merely a press fit connection.

31 Claims, 8 Drawing Sheets

(51) Int. Cl.
  *B29C 65/36* (2006.01)
  *B29C 65/06* (2006.01)
  *B29C 65/08* (2006.01)
  *B29C 65/14* (2006.01)
  *B29C 65/16* (2006.01)
  *B29C 65/18* (2006.01)
  *B29C 65/48* (2006.01)
  *B29C 65/56* (2006.01)
  *B29L 31/14* (2006.01)
  *B29L 31/00* (2006.01)

(52) U.S. Cl.
  CPC ....... *B01D 46/008* (2013.01); *B01D 46/0097* (2013.01); *B29C 65/06* (2013.01); *B29C 65/08* (2013.01); *B29C 65/1425* (2013.01); *B29C 65/16* (2013.01); *B29C 65/18* (2013.01); *B29C 65/36* (2013.01); *B29C 65/48* (2013.01); *B29C 65/56* (2013.01); *A61M 2205/7536* (2013.01); *A61M 2207/00* (2013.01); *B29K 2023/06* (2013.01); *B29L 2031/14* (2013.01); *B29L 2031/753* (2013.01)

(58) Field of Classification Search
  CPC .. B01D 46/008; B01D 46/0097; B29C 65/06; B29C 65/08; B29C 65/1425; B29C 65/16; B29C 65/18; B29C 65/36; B29C 65/48; B29C 65/56; B29L 2031/14; B29L 2031/753; B29K 2023/06
  See application file for complete search history.

(56) References Cited

U.S. PATENT DOCUMENTS

| | | | |
|---|---|---|---|
| 4,354,571 A | 10/1982 | Lakin et al. | |
| 4,384,580 A | 5/1983 | Leviton | |
| 4,411,661 A | 10/1983 | Kersten | |
| 4,487,606 A * | 12/1984 | Leviton | A61M 1/0052 141/59 |
| 4,630,847 A | 12/1986 | Blenkush | |
| 4,863,446 A | 9/1989 | Parker | |
| 5,266,233 A | 11/1993 | Houghton et al. | |
| 5,280,963 A | 1/1994 | Schober et al. | |
| 5,363,745 A | 11/1994 | Lin et al. | |
| 5,384,092 A | 1/1995 | Sawhill et al. | |
| 5,624,417 A | 4/1997 | Cook et al. | |
| 5,723,870 A | 3/1998 | Crowne et al. | |
| 5,792,126 A | 8/1998 | Tribastone et al. | |
| 5,795,475 A | 8/1998 | Luedke et al. | |
| 5,997,733 A | 12/1999 | Wilbur et al. | |
| 6,056,731 A | 5/2000 | Koetke et al. | |
| 6,123,093 A | 9/2000 | D'antonio et al. | |
| 6,175,779 B1 | 1/2001 | Barrett | |
| 6,263,887 B1 | 7/2001 | Dunn | |
| 6,588,436 B2 | 7/2003 | Dunn et al. | |
| 6,776,175 B2 | 8/2004 | Dunn et al. | |
| 6,784,443 B2 | 8/2004 | Pennington et al. | |
| 6,796,317 B2 | 9/2004 | Dunn et al. | |
| 6,800,074 B2 | 10/2004 | Henley et al. | |
| 6,893,425 B2 | 5/2005 | Dunn et al. | |
| 6,902,673 B2 | 6/2005 | Smit et al. | |
| 7,082,969 B1 | 8/2006 | Hollerback et al. | |
| 7,090,663 B2 | 8/2006 | Dunn et al. | |
| 7,163,618 B2 | 1/2007 | Beckham et al. | |
| 7,258,711 B2 | 8/2007 | Dunn et al. | |
| 7,261,701 B2 | 8/2007 | Davis et al. | |
| 7,497,340 B2 | 3/2009 | Hershberger et al. | |
| 7,615,037 B2 | 11/2009 | Murray et al. | |
| 8,088,291 B2 | 1/2012 | Hershberger et al. | |
| 8,292,857 B2 | 10/2012 | Martini et al. | |
| D678,502 S | 3/2013 | Schmidt et al. | |
| D678,504 S | 3/2013 | Schmidt et al. | |
| 8,449,510 B2 | 5/2013 | Martini et al. | |
| 8,827,969 B2 | 9/2014 | Martini et al. | |
| 9,089,629 B2 | 7/2015 | Martini et al. | |
| 9,375,520 B2 | 6/2016 | Martini et al. | |
| 9,662,426 B2 | 5/2017 | Martini et al. | |
| 10,188,775 B2 | 1/2019 | Martini et al. | |
| 2003/0144422 A1 | 7/2003 | Honeycutt et al. | |
| 2005/0139532 A1 | 6/2005 | Hershberger et al. | |
| 2005/0143685 A1 | 6/2005 | Peyron et al. | |
| 2005/0171495 A1 | 8/2005 | Austin et al. | |
| 2005/0189288 A1 * | 9/2005 | Hershberger | A61M 1/0056 210/448 |
| 2007/0028570 A1 | 2/2007 | Dunn et al. | |
| 2007/0135779 A1 | 6/2007 | Lalomia et al. | |
| 2007/0208151 A1 | 9/2007 | Okada et al. | |
| 2008/0179344 A1 | 7/2008 | Michaels et al. | |
| 2009/0012493 A1 * | 1/2009 | Harig | A61M 1/0003 604/404 |
| 2011/0108474 A1 * | 5/2011 | Folden | A61M 1/3627 210/188 |
| 2011/0277851 A1 | 11/2011 | Martini et al. | |
| 2011/0278296 A1 | 11/2011 | Martini et al. | |
| 2017/0246358 A1 | 8/2017 | Martini et al. | |

FOREIGN PATENT DOCUMENTS

| | | |
|---|---|---|
| DE | 202006012253 | 12/2006 |
| EP | 2044964 | 9/2016 |
| WO | 9640309 | 12/1996 |
| WO | 9900154 | 1/1999 |
| WO | 2006019406 | 2/2006 |

OTHER PUBLICATIONS

"European Application Serial No. 16189730.1, Response filed May 13, 2019 to Communication Pursuant to Article 94(3) EPC dated Jan. 2, 2019", 43 pgs.
"U.S. Appl. No. 13/188,048, Non Final Office Action dated Jul. 2, 2015", 14 pgs.
"U.S. Appl. No. 13/188,048, Response filed Oct. 29, 2015 to Non Final Office Action dated Jul. 2, 2015", 8 pgs.
"U.S. Appl. No. 13/188,048, Non Final Office Action dated Apr. 25, 2014", 11 pgs.
"U.S. Appl. No. 13/188,048, Response filed Jun. 12, 2014 to Non Final Office Action dated Apr. 25, 2014", 12 pgs.
"U.S. Appl. No. 13/188,048, Final Office Action dated Oct. 14, 2014", 14 pgs.
"U.S. Appl. No. 13/188,048, Response filed Dec. 5, 2014 to Final Office Action dated Oct. 14, 2014", 12 pgs.
"U.S. Appl. No. 13/188,048, Advisory Action dated Feb. 6, 2015", 3 pgs.
"U.S. Appl. No. 13/188,048, Response filed Apr. 2, 2015 to Advisory Action dated Feb. 6, 2015", 15 pgs.
"Canadian Application Serial No. 2,640,549, Office Action dated Jul. 7, 2015", 4 pgs.
"U.S. Appl. No. 13/188,117, Non Final Office Action dated Jan. 29, 2016", 14 pgs.
"U.S. Appl. No. 13/188,048, Notice of Allowance dated Feb. 29, 2016", 10 pgs.
"U.S. Appl. No. 13/188,048, Corrected Notice of Allowance dated Mar. 21, 2016", 4 pgs.
"U.S. Appl. No. 13/188,117, Non Final Office Action dated Mar. 11, 2013", 9 pgs.
"U.S. Appl. No. 13/188,117, Final Office Action dated Nov. 8, 2013", 12 pgs.
"U.S. Appl. No. 13/188,117, Advisory Action dated Jan. 29, 2014", 2 pgs.
"U.S. Appl. No. 13/188,117, Non Final Office Action dated Apr. 21, 2014", 11 pgs.
"U.S. Appl. No. 13/188,117, Final Office Action dated Oct. 14, 2014", 12 pgs.
"U.S. Appl. No. 13/188,117, Advisory Action dated Jan. 8, 2015", 2 pgs.
"U.S. Appl. No. 13/188,117, Response filed Jul. 21, 2016 to Non Final Office Action dated Jan. 29, 2016", 9 pgs.

(56) References Cited

OTHER PUBLICATIONS

"European Application Serial No. 08165948.4, Extended European Search Report dated Nov. 16, 2011", 8 pgs.

"European Application Serial No. 08165948.4, The partial European search report dated May 18, 2011", 5 pgs.

"European Application Serial No. 08165948.4, Intention to grant dated Apr. 1, 2016", 68 pgs.

"U.S. Appl. No. 13/188,117, Final Office Action dated Oct. 31, 2016", 10 pgs.

"U.S. Appl. No. 13/188,117, Response filed Jun. 10, 2013 to Non Final Office Action dated Mar. 11, 2013", 7 pgs.

"U.S. Appl. No. 13/188,117, Response filed Jan. 7, 2014 to Final Office Action dated Nov. 8, 2013", 11 pgs.

"U.S. Appl. No. 13/188,117, Response filed Feb. 7, 2014 to Advisory Action dated Jan. 29, 2014", 8 pgs.

"U.S. Appl. No. 13/188,117, Response filed Jun. 25, 2014 to Non Final Office Action dated Apr. 21, 2014", 8 pgs.

"U.S. Appl. No. 13/188,117, Response filed Dec. 2, 2014 to Final Office Action dated Oct. 14, 2014", 8 pgs.

"U.S. Appl. No. 13/188,117, Response filed Mar. 2, 2015 to Advisory Action dated Jan. 8, 2015", 11 pgs.

"U.S. Appl. No. 13/188,117, Response filed Jan. 24, 2017 to Final Office Action dated Oct. 31, 2016", 11 pgs.

"U.S. Appl. No. 13/188,117, Examiner Interview Summary dated Jan. 26, 2017", 3 pgs.

"U.S. Appl. No. 13/188,117, Notice of Allowance dated Mar. 10, 2017", 7 pgs.

"U.S. Appl. No. 13/188,117, Response filed Mar. 23, 2017 to Notice of Allowance dated Mar. 10, 2017", 10 pgs.

"U.S. Appl. No. 13/188,117, Notice of Allowance dated Apr. 11, 2017", 8 pgs.

"U.S. Appl. No. 15/496,392, Preliminary Amendment filed May 24, 2017", 7 pgs.

"European Application Serial No. 16189730.1, Extended European Search Report dated Aug. 24, 2017", 7 pgs.

"Canadian Application Serial No. 2,945,389, Office Action dated Oct. 6, 2017", 3 pgs.

"Canadian Application Serial No. 2,945,389, Response filed Apr. 11, 2018 to Office Action dated Oct. 6, 2017", 7 pgs.

"European Application Serial No. 16189730.1, Response filed Apr. 18, 2018 to Office Action dated Oct. 23, 2017", 19 pgs.

Dornoch Medical Systems, Inc., "", Transposal—Nothing touches it—Collection options for Clinical Flexibility, Facility-Wide Infectious Fluid Waste Management System, Dornoch, Riverside, Missouri, 64150, Brochure, at least as early as Jun. 2010, 2 pgs.

"European Application Serial No. 16189730.1, Communication Pursuant to Article 94(3) EPC dated Jan. 2, 2019", 4 pgs.

"U.S. Appl. No. 15/496,392, Non Final Office Action dated Jul. 12, 2018", 8 pgs.

U.S. Appl. No. 12/245,966 U.S. Pat. No. 8,292,857, filed Oct. 6, 2008, Medical Waste Fluid Collection and Disposal System.

U.S. Appl. No. 13/188,048 U.S. Pat. No. 9,375,520, filed Jul. 21, 2011, Medical Waste Fluid Collection and Disposal System.

U.S. Appl. No. 13/188,067 U.S. Pat. No. 9,089,629, filed Jul. 21, 2011, Lid Assembly for a Medical Waste Fluid Collection and Disposal System.

U.S. Appl. No. 13/188,036 U.S. Pat. No. 8,827,969, filed Jul. 21, 2011, Medical Waste Fluid Collection and Disposal System.

U.S. Appl. No. 13/188,058 U.S. Pat. No. 8,449,510, filed Jul. 21, 2011, Lid Assembly for a Medical Waste Fluid Collection and Disposal.

U.S. Appl. No. 15/496,392 U.S. Pat. No. 10,188,775, filed Apr. 25, 2017, Lid for a Medical Waste Fluid Collection and Disposal System.

U.S. Appl. No. 13/188,117 U.S. Pat. No. 9,662,426, filed Jul. 21, 2011, Lid for a Medical Waste Fluid Collection and Disposal System.

\* cited by examiner

HIGH FLOW MANIFOLD

FIELD

The present disclosure relates to high flow manifolds for collecting and disposing of medical waste.

BACKGROUND

Various forms of liquid medical wastes are commonly produced in surgery and other medical procedures. Such wastes may include blood and other body fluids of patients. The wastes may also include solid particles such as fragments of bone or cartilage. Some procedures produce a high volume of such waste from a single patient. For example, saline solution is used to irrigate the knee area during arthroscopic procedures. As another example, saline solution is used to flush the bladder, urethra and/or prostate in some urology procedures. Such procedures may produce as much as 30,000 cc of liquid medical waste.

Liquid medical waste generates significant disposal problems due to its possible contamination with various infectious diseases, including AIDS, hepatitis and MRSA. As a result, rules and regulations for the handling and disposal of liquid medical waste have been imposed by various governmental and regulatory agencies. For example, new regulations require the use of engineering controls to protect employees from exposure. In addition, hospitals and other health care facilities have been searching for methods and systems that reduce hospital personnel's exposure to the fluids during collection, handling and disposal. Procedures that produce large volumes of liquid medical waste amplify these issues and concerns.

Various systems and methods have been used for collecting, handling and disposing of fluids from procedures that produce large volumes of liquid medical waste. The collection vessels vary from simple buckets to automated, electronically controlled processing equipment.

Systems comprising a vacuum source and suction canisters are commonly used to aspirate fluids from patients during surgical procedures. Such suction canisters can range in volume from around 1200 cc to around 3000 cc. A suction canister can feature a removable lid or manifold with a vacuum port and a patient or suction port. During a surgical procedure, the vacuum port is connected by flexible tubing to a hospital vacuum source while the suction port is connected by a second flexible tube to the region of the patient from which the fluid wastes are collected. The removable manifold can have a filter associated with the vacuum port that can increase the safety of systems employing suction canisters by shutting off a canister's vacuum supply when wet and preventing contamination of the vacuum supply system. Conversely, such filters also limit flow performance of the manifold.

SUMMARY

The present inventors have recognized, among other things, that a problem to be solved can include the need for single-use manifolds for medical waste fluid collection systems that have more secure filters and that increase flow performance without additional cost. The present subject matter can help provide a solution to this problem, such as by providing a system for guiding medical waste fluid into a medical waste collection canister, the system comprising a manifold and a filter. The manifold can comprise a top surface and a sidewall extending from the top surface in a first direction. The top surface and the sidewall can define an interior chamber of the manifold. The top surface can comprise an inlet port and a vacuum port disposed therein. The inlet port can be configured to connect to a source of medical waste fluid. The vacuum port can be configured to connect to a vacuum source. The manifold can be formed from a first polymer. The filter can be positioned within the interior chamber of the manifold and immediately upstream of the vacuum port so as to filter air flowing into the vacuum port. The filter can extend away from the top surface of the manifold in the first direction and the filter can be formed from a second polymer. The filter can be fused to a surface of the interior chamber of the manifold or a peripheral surface of the vacuum port so as to form a fused interface, and not merely a press fit connection. In other words, the filter is securely held in place within the chamber by fusion of the materials rather than pressure/force between the components.

The present description also provides for a device that can be formed by a process comprising the steps of providing or obtaining a manifold, the manifold comprising a top surface and a sidewall extending from the top surface in a first direction, the manifold defining a manifold chamber, the top surface comprising an inlet port and a vacuum port disposed therein, the inlet port configured to connect to a source of medical waste fluid, the vacuum port configured to connect to a vacuum source, the manifold formed from a first polymer; providing or obtaining a filter formed from a second polymer, wherein the filter and a circumferential surface of the vacuum port are rotationally symmetric with respect to each other; and rotating the one of the filter and the manifold relative to the other to fuse the filter and the manifold along a fused interface.

The present description also provides for a method that can comprise the steps of removing a first filter from a manifold, the manifold comprising: a manifold housing comprising a top surface and a sidewall extending from the top surface in a first direction, the manifold housing defining a manifold chamber, the top surface comprising an inlet port and a vacuum port disposed therein, the inlet port configured to connect to a source of medical waste fluid, the vacuum port configured to connect to a vacuum source, the manifold housing formed from a first polymer; the first filter coupled to and in communication with the vacuum port and extending away from the top surface in the first direction; washing the manifold; disinfecting the manifold; and coupling a second filter to the vacuum port to form a recycled manifold.

This overview is intended to provide an overview of subject matter of the present patent application. It is not intended to provide an exclusive or exhaustive explanation of the invention. The detailed description is included to provide further information about the present patent application.

DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
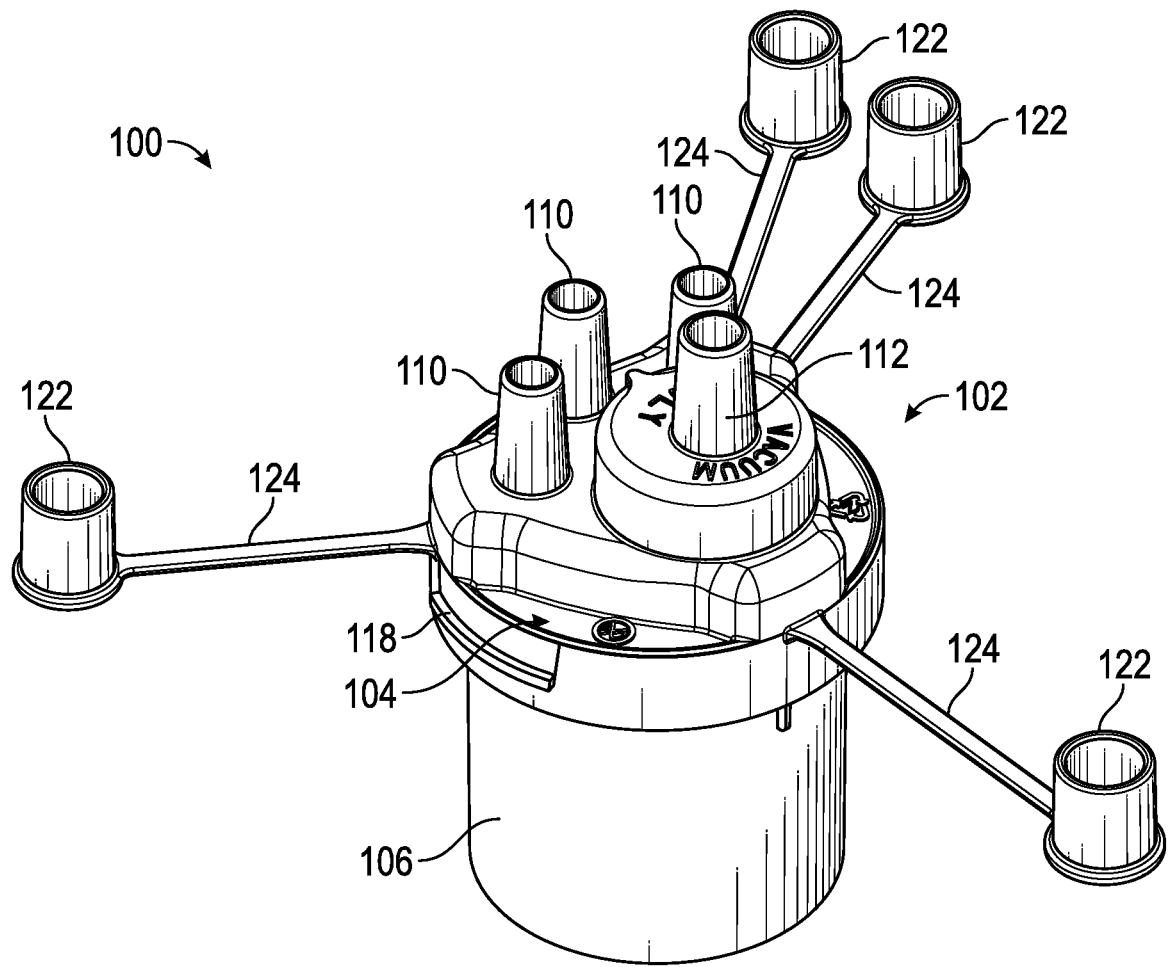
FIG. 1 provides a top perspective view of an exemplary system according to the present subject matter.
Figure 2:
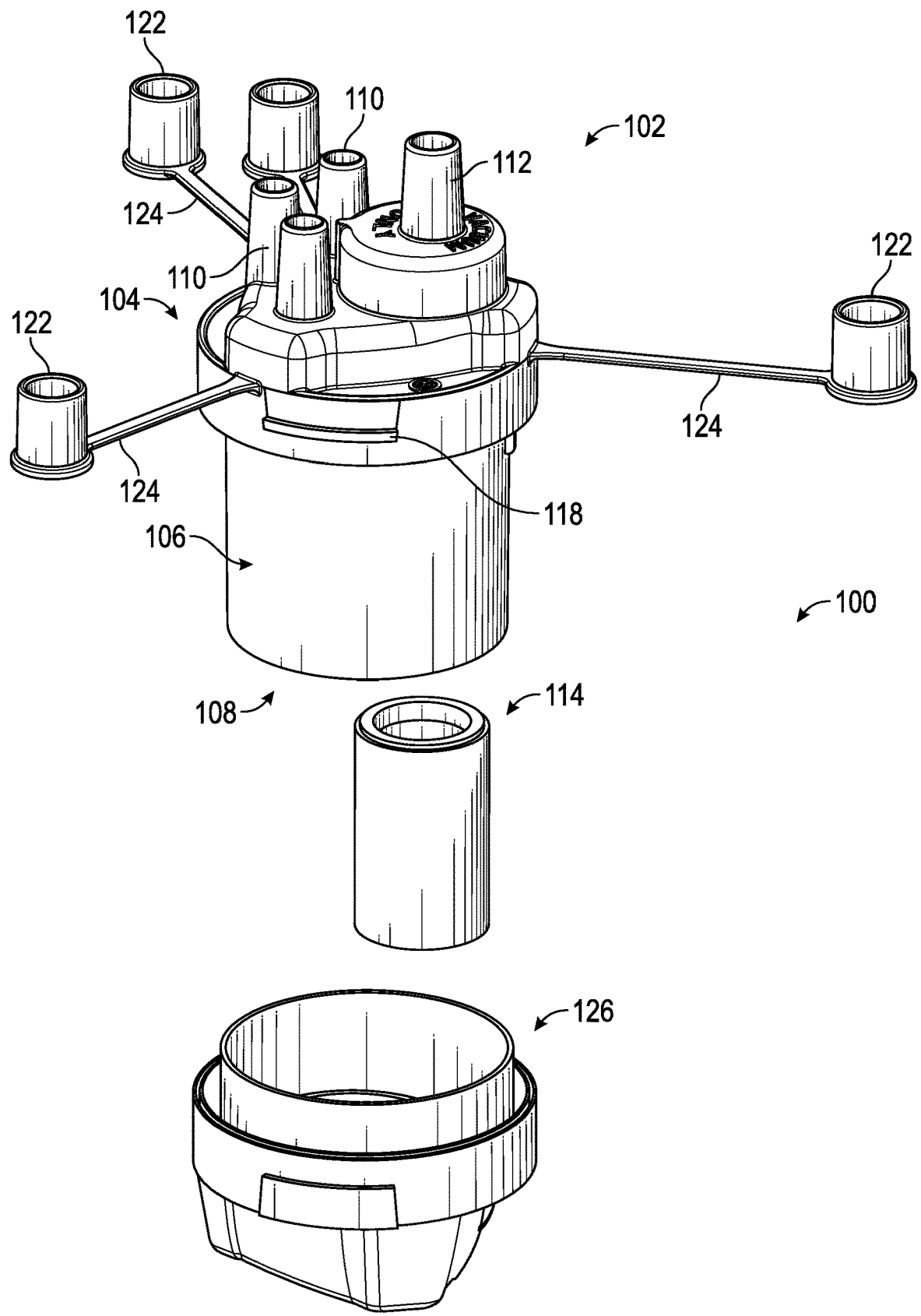
FIG. 2 provides an exploded view of the system of FIG. 1.
Figure 3:
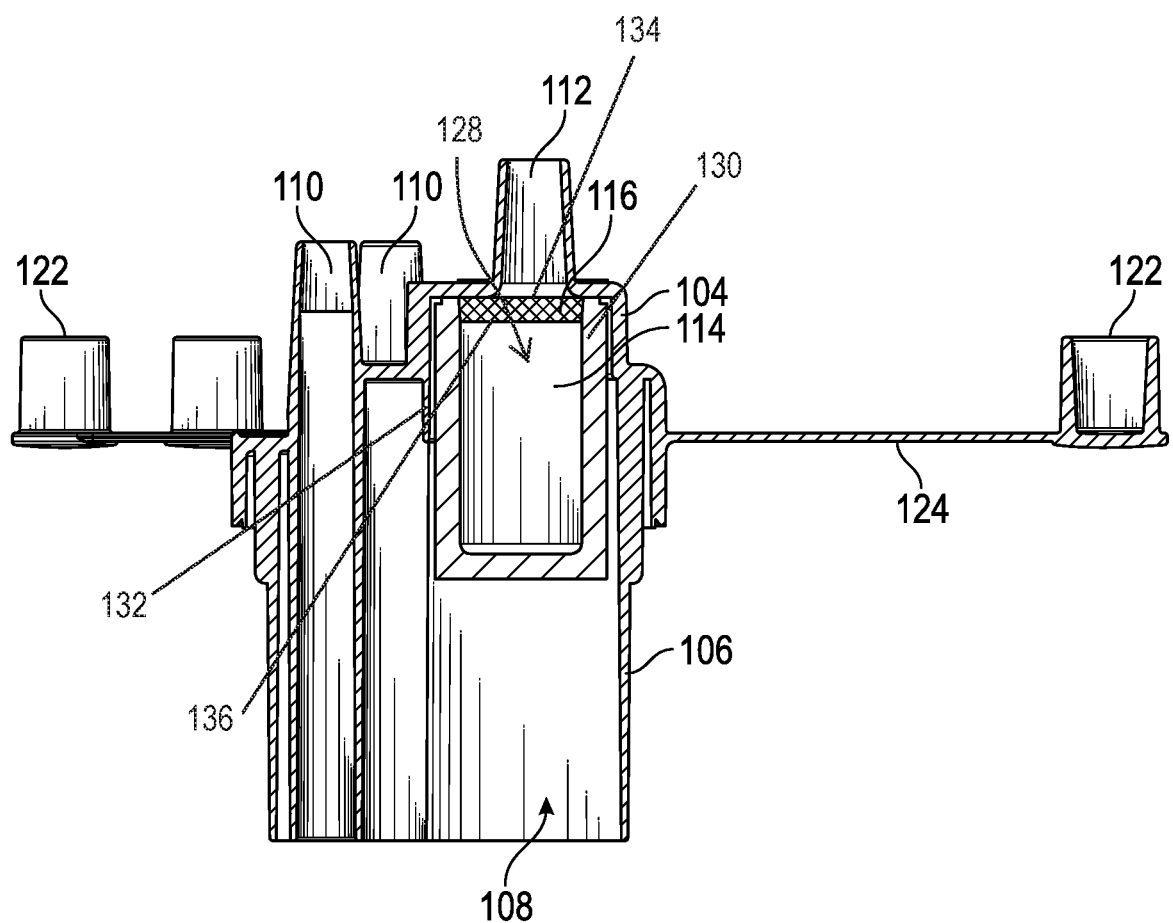
FIG. 3 provides a side cross-sectional view of the system of FIG. 1.
Figure 4:
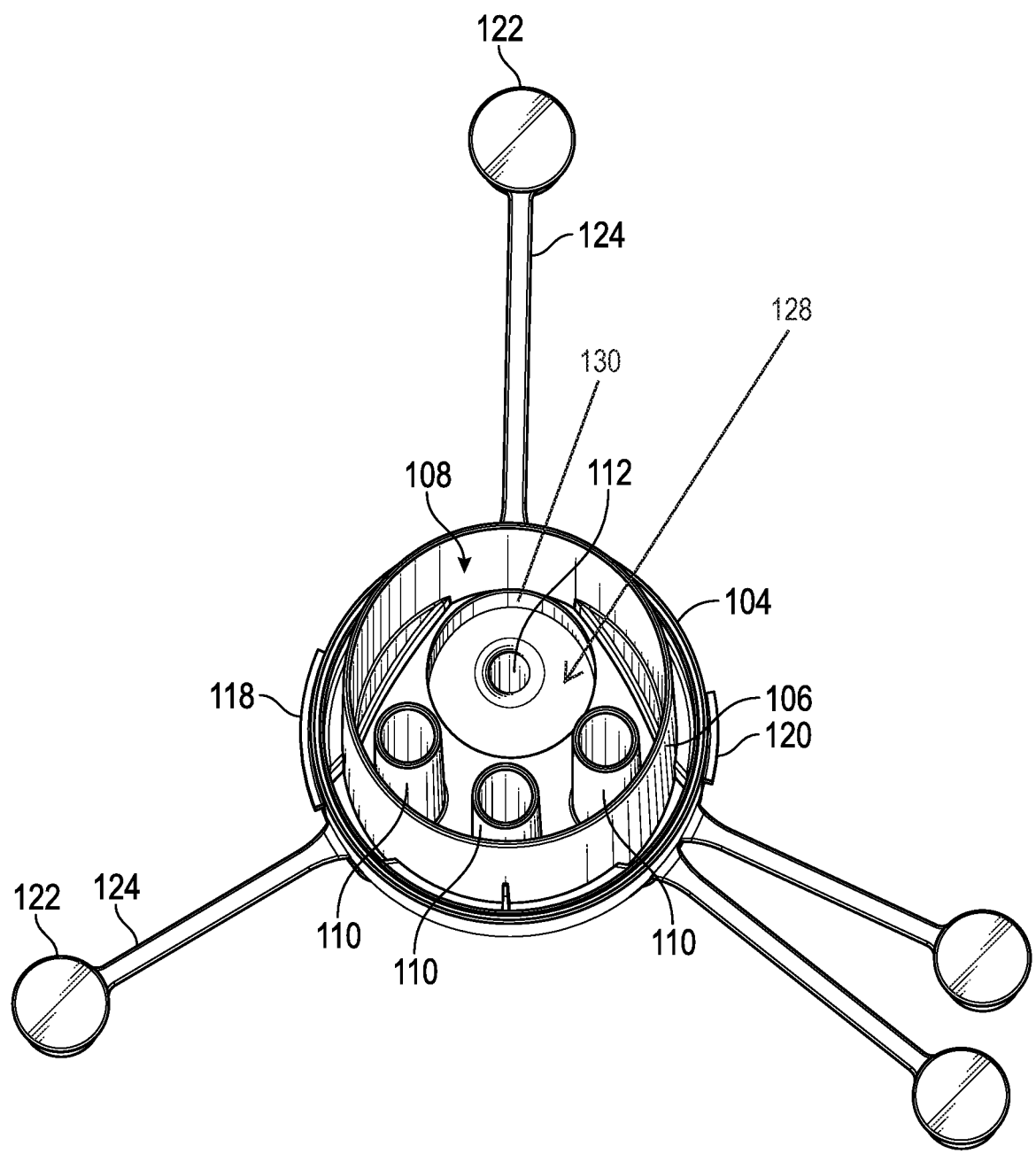
FIG. 4 provides a bottom perspective view of the system of FIG. 1 without a filter installed.
Figure 5:
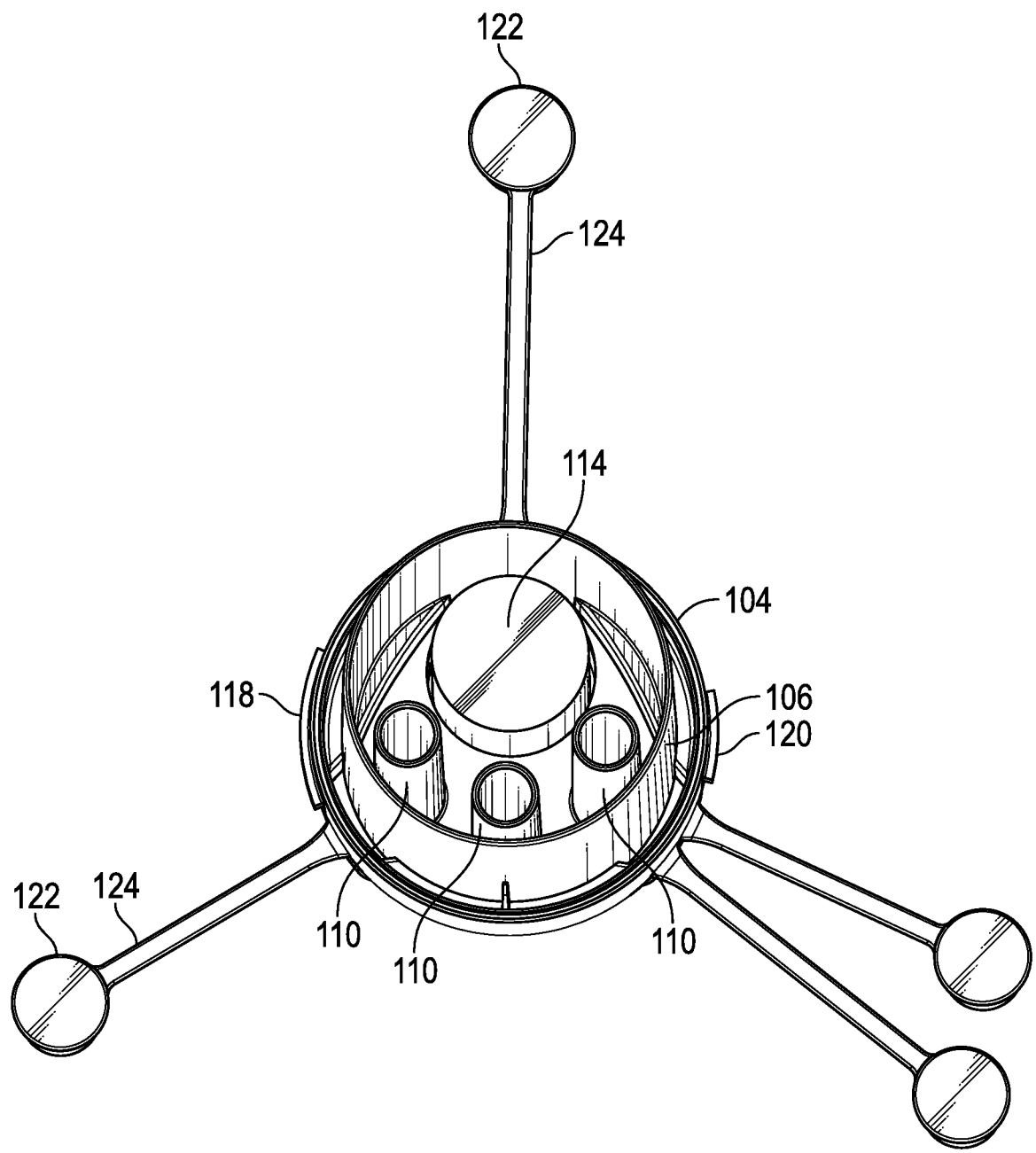
FIG. 5 provides a bottom perspective view of the system of FIG. 1 with a filter installed.
Figure 6:
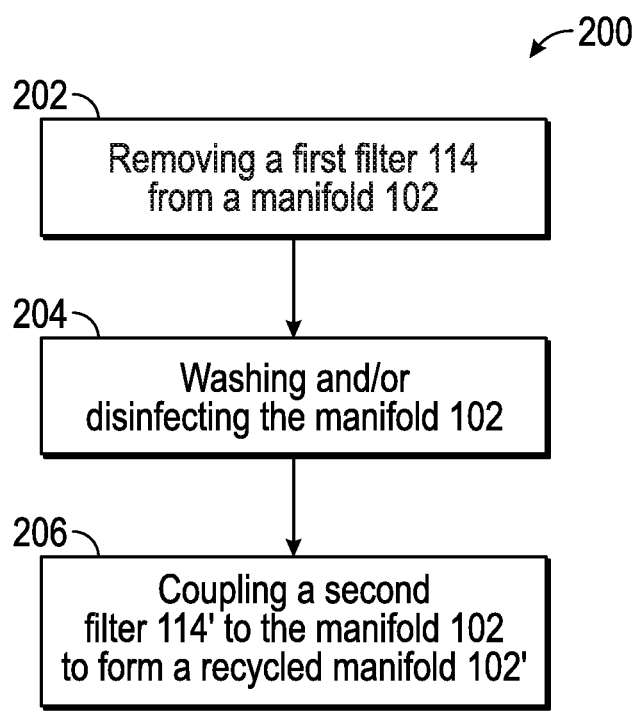
FIG. 6 is a flow chart illustrating an exemplary method for reprocessing or recycling a manifold according to the present subject matter.

The present description relates to a system 100 for guiding medical waste fluid into a medical waste collection canister. As illustrated in the various views of FIGS. 1-5, the system 100 can comprise a manifold 102 and a filter 114. The manifold 102 can comprise a top surface 104 and a sidewall 106 extending from the top surface 104 in a first direction. The top surface 104 and the sidewall 106 can define an interior chamber 108 of the manifold 102. The top surface 104 can comprise an inlet port 110 and a vacuum port 112 disposed therein. The inlet port 110 can be configured to connect to a source of medical waste fluid. The inlet port 110 can comprise a plurality of inlet ports. The vacuum port 112 can be configured to connect to a vacuum source. The manifold 102 can be formed from a first polymer. At least one, and optionally each, of the inlet port 110 and vacuum port 112 can comprise a cap 122 removably securable thereto. The cap 122 can be coupled to the manifold 102 via a tether 124. The system 100 can further comprise a manifold cap 126 that is removably coupleable to the free end of the sidewall 106. The system 100 is adapted to be secured to the medical waste collection canister, and the canister is coupled to a fluid waste collection cart/station.

A filter 114 can be positioned within the interior chamber 108 of the manifold 102 and immediately upstream of the vacuum port 112 so as to filter air flowing into the vacuum port 112. Manifold 102 can include socket 128 for receiving filter 114. Socket 125 can be formed by wall portion 130 and flange 132. The filter 114 can extend away from the top surface 104 of the manifold 102 in the first direction and the filter 114 can be formed from a second polymer. The filter can be a hygroscopic filter or the like. The inlet port 110 can extend from the top surface 104 of the manifold 102 in the first direction a distance greater than the filter 114 extends from the top surface 104 in the same direction. The manifold 102 can lack any housing extending away from the top surface 104 of the manifold 102 adapted to house any portion of the filter. The manifold 120 can lack any features to mechanically couple the filter 114 thereto such as, for example and without limitation, rings, ribs, threads, tabs, bayonet mounts, and the like. As such, the filter 114 is entirely exposed to the interior chamber 108 except at the fused interface 116 and does not move with respect to the manifold 102 when the manifold is attached to the canister. The fused interface 116 can be proximate the top filter surface 134 and spaced from the bottom filter surface 136.

In one example, the first polymer or the second polymer can comprise a thermoplastic polymer. In a further aspect, the first polymer or the second polymer can comprise polyethylene. In an additional or alternative aspect, the first polymer can comprise high density polyethylene and the second polymer can comprise super high density polyethylene. High density polyethylene and super high density polyethylene can be substantially similar materials.

The filter 114 can be fused to a surface of the interior chamber 108 of the manifold 102 or a peripheral surface of the vacuum port 112 so as to form a fused interface 116, and not merely a press fit connection. The fused interface 116 can be one or more of circular, radially symmetric, or irregular. The fused interface 116 can comprise a chemical bond between the first polymer and the second polymer. Additionally or alternatively, the fused interface 116 can be formed by fusion and, more particularly, heating at least a portion of the filter 114, at least a portion of the manifold 102, or a portion of each of the filter 114 and manifold 102 to a viscous state and physically causing the polymer chains to interdiffuse, such diffusion optionally being facilitated via the application of pressure. The fused interface 116 can be formed by processes such as, but not limited to, direct heating, induced heating, and frictional heating. Direct heating can include heated tool welding, hot plate welding, resistance welding, infrared welding, laser welding, and the like. Induced heating can include induction welding, radiofrequency welding, microwave welding, and the like. Frictional heating can include ultrasonic welding, vibration welding, spin welding, and the like. In one example, the fused interface can be a hermetic interface.

Figure 7:
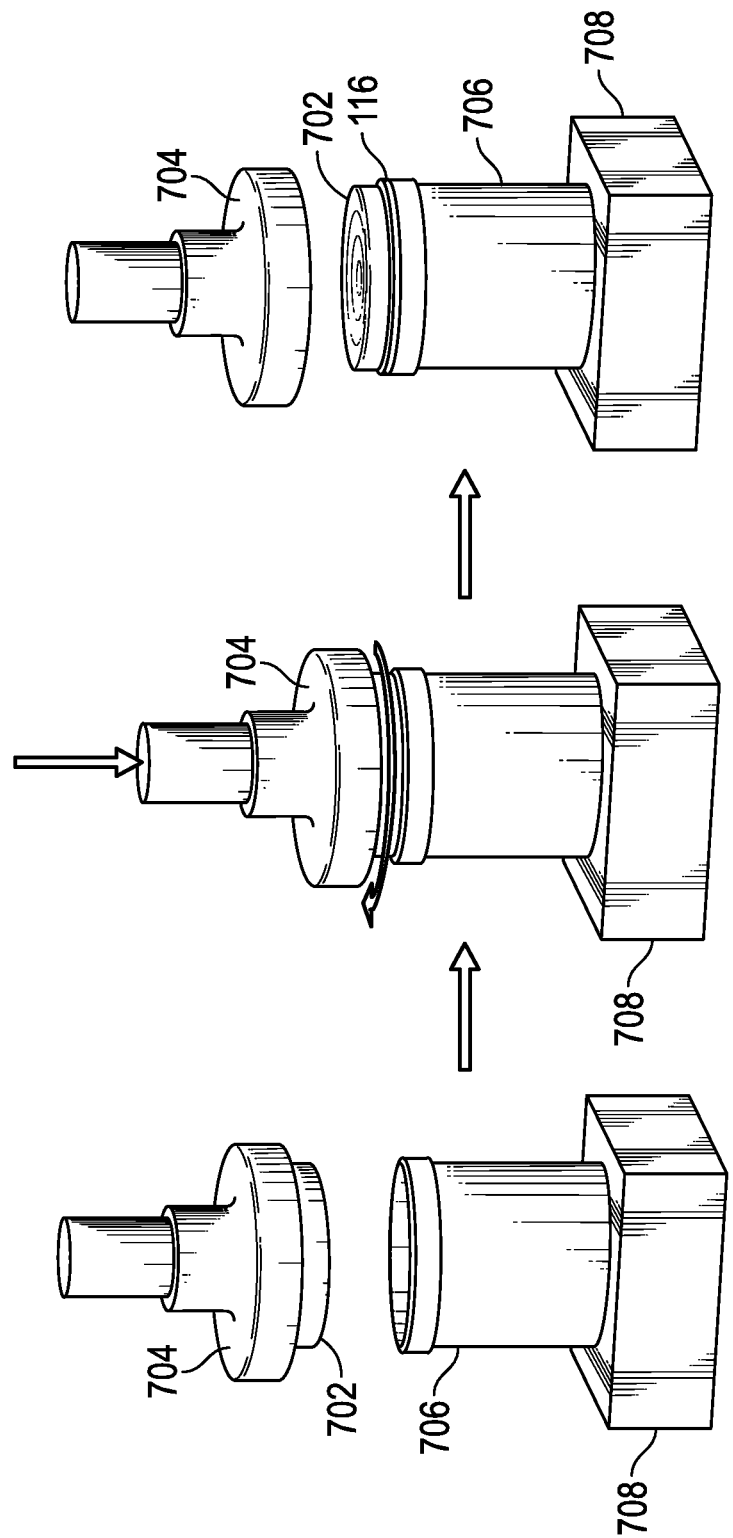
FIG. 7 is a schematic showing one example of spin welding of a first part and a second part according to the present subject matter.
Figure 8:
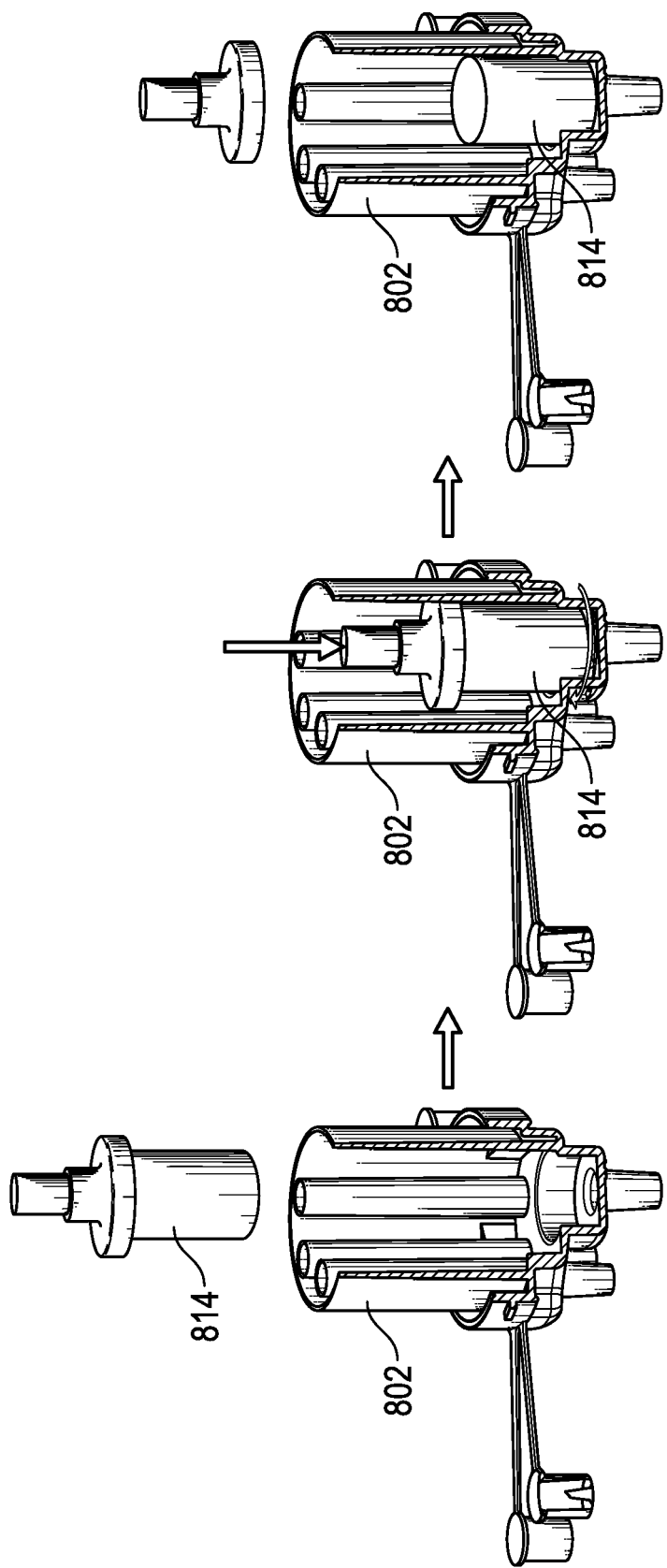
FIG. 8 is a schematic showing one example of spin welding a filter and a manifold according to the present subject matter.

In one example illustrated in FIGS. 7 and 8, the fused interface can be formed by spin welding the filter to the manifold. Spin welding can comprise rapid rotation of a first part 702 comprising a first polymer and coupled to a spinning tool 704 with respect to a second part 706 comprising a second polymer and coupled to a stationary fixture 708 to form a fused interface 116 and join the first part 702 and the second part 706. In one example, spin welding comprises a process that fuses a cylindrical thermoplastic filter (e.g., filter 814) to a manifold (e.g., manifold 802) by spinning the circular filter rapidly against the manifold, or vice versa. The inventors have successfully fused a filter 814 to a manifold 802 by spin welding the filter material and the manifold material and achieved a strong bond or connection between the filter 814 and the manifold 802 that was stronger than a press-fit or friction-fit connection. Removing the filter 814 required the fused connection or interface to be broken in order to be removed. Also, the filter 814 was not damaged by the welding process. (FIG. 8 does not show the stationary fixture to secure the manifold during the spin welding operation.)

In an additional or alternative example, the manifold 102 and the filter 114 can be monolithic such that the manifold 102 and the filter 114 are fused to form a unitary structure that comprises substantially the same composition throughout. Here, the fused interface 116 would not be substantially different than any other portion of the filter 114 or the manifold 102 as the manifold 102 and the filter 114 are formed from materials that are at least substantially similar.

The manifold 102 can further comprise a fastener for coupling the manifold to a canister or the like. To this end, the manifold can comprise a first tab 118 and, optionally, a second tab 120 extending radially outward from a circumferential edge of the manifold. The first tab 118 and the second tab 120 can be spaced apart along the circumferential edge of the manifold. The first tab 118 and the second tab 120 can comprise a bayonet mount.

The present description also provides for a device that can be formed by a process comprising the steps of providing or obtaining a manifold 102, the manifold 102 comprising a top surface 104 and a sidewall 106 extending from the top surface 104 in a first direction, the manifold 102 defining a manifold chamber 108, the top surface 104 comprising an inlet port 110 and a vacuum port 112 disposed therein, the inlet port 110 configured to connect to a source of medical waste fluid, the vacuum port 112 configured to connect to a vacuum source, the manifold 102 formed from a first polymer; providing or obtaining a filter 114 formed from a second polymer, wherein the filter 114 and a circumferential surface of the vacuum port 112 are rotationally symmetric with respect to each other; and rotating the one of the filter 114 and the manifold 102 relative to the other to fuse the filter 114 and the manifold 102 along a fused interface 116.

The present description also provides for a method 200 that can comprise the following steps: step 202 of removing a first filter from a manifold, the manifold 102 comprising: a manifold housing comprising a top surface 104 and a sidewall 106 extending from the top surface 104 in a first direction, the manifold housing defining a manifold chamber 108, the top surface 104 comprising an inlet port 110 and a vacuum port 112 disposed therein, the inlet port 110 configured to connect to a source of medical waste fluid, the vacuum port 112 configured to connect to a vacuum source, the manifold housing formed from a first polymer; the first filter 114 coupled to and in communication with the vacuum port 112 and extending away from the top surface 104 in the first direction; step 204 of washing the manifold 102 and/or disinfecting the manifold 102; and step 206 of coupling a second filter 114' to the vacuum port to form a recycled manifold 102'. The first filter 114 can be fused to the manifold 102 and removing the first filter 114 from the manifold 102 can comprise severing the first filter 114 from the manifold 102 or otherwise breaking a fused interface 116 between the first filter 114 and the manifold 102.

VARIOUS NOTES & EXAMPLES

Example 1 is a system for guiding medical waste fluid into a medical waste collection canister, the system comprising a manifold and a filter. The manifold can comprise a top surface and a sidewall extending from the top surface in a first direction. The top surface and the sidewall can define an interior chamber of the manifold. The top surface can comprise an inlet port and a vacuum port disposed therein. The inlet port can be configured to connect to a source of medical waste fluid. The vacuum port can be configured to connect to a vacuum source. The manifold can be formed from a first polymer. The filter can be positioned within the interior chamber of the manifold and immediately upstream of the vacuum port so as to filter air flowing into the vacuum port. The filter can extend away from the top surface of the manifold in the first direction and the filter can be formed from a second polymer. The filter can be fused to a surface of the interior chamber of the manifold or a peripheral surface of the vacuum port so as to form a fused interface, and not merely a press fit connection.

In Example 2, the subject matter of Example 1 can optionally include wherein the fused interface comprises a chemical bond between the first polymer and the second polymer.

In Example 3, the subject matter of any one or more of Examples 1-2 can optionally include wherein the fused interface is formed by melting a portion of the filter to bond the second polymer to the manifold.

In Example 4, the subject matter of any one or more of Examples 1-3 can optionally include wherein the fused interface is formed by spin welding, hot plate welding, laser welding, or radio frequency welding.

In Example 5, the subject matter of any one or more of Examples 1-4 can optionally include wherein the fused interface is formed by spin welding the filter to the manifold, spin welding comprising rapid rotation of the filter and the manifold with respect to each other, so as to melt and chemically bond the first polymer and the second polymer.

In Example 6, the subject matter of any one or more of Examples 1-5 can optionally include wherein the inlet port extends from the top surface of the manifold in the first direction a distance greater than the filter extends from the top surface of the manifold in the first direction.

In Example 7, the subject matter of any one or more of Examples 1-6 can optionally include wherein the fused interface comprises a hermetic interface.

In Example 8, the subject matter of any one or more of Examples 1-7 can optionally include wherein the first polymer or the second polymer is a thermoplastic polymer.

In Example 9, the subject matter of Example 8 can optionally include wherein the first polymer or the second polymer comprises polyethylene.

In Example 10, the subject matter of Example 9 can optionally include wherein the first polymer and the second polymer comprise polyethylene.

In Example 11, the subject matter of any one or more of Examples 1-10 can optionally include wherein the filter is a hygroscopic filter.

In Example 12, the subject matter of any one or more of Examples 1-11 can optionally include wherein the manifold and the filter are monolithic.

In Example 13, the subject matter of any one or more of Examples 1-12 can optionally include wherein a fused interface of the filter and peripheral surface of the vacuum port is circular.

In Example 14, the subject matter of any one or more of Examples 1-13 can optionally include wherein the manifold further comprises a first tab extending radially outward from a circumferential edge of the manifold.

In Example 15, the subject matter of Example 14 can optionally include wherein the manifold further comprises a second tab extending radially outward from the circumferential edge of the manifold, wherein the first tab and the second tab are spaced apart along the circumferential edge of the manifold.

In Example 16, the subject matter of Example 15 can optionally include wherein the first tab and the second tab comprise a bayonet mount.

In Example 17, the subject matter of any one or more of Examples 1-16 can optionally include wherein the inlet port further comprises a plurality of inlet ports.

In Example 18, the subject matter of any one or more of Examples 1-17 can optionally include wherein the inlet port or the vacuum port further comprises a cap removably securable thereto.

In Example 19, the subject matter of any one or more of Examples 1-18 can optionally include wherein the cap is coupled to the manifold via a tether.

Example 20 is a device that can be formed by a process comprising the steps of providing or obtaining a manifold, the manifold comprising a top surface and a sidewall extending from the top surface in a first direction, the manifold defining a manifold chamber, the top surface comprising an inlet port and a vacuum port disposed therein, the inlet port configured to connect to a source of medical waste fluid, the vacuum port configured to connect to a vacuum source, the manifold formed from a first polymer; providing or obtaining a filter formed from a second polymer, wherein the filter and a circumferential surface of the vacuum port are rotationally symmetric with respect to each other; and rotating the one of the filter and the manifold relative to the other to fuse the filter and the manifold along a fused interface.

In Example 21, the subject matter of Example 20 can optionally include wherein the first polymer or the second polymer is a thermoplastic polymer.

In Example 22, the subject matter of Example 21 can optionally include wherein the first polymer or the second polymer comprises polyethylene.

In Example 23, the subject matter of Example 22 can optionally include wherein the first polymer and the second polymer comprise polyethylene.

In Example 24, the subject matter of any one or more of Examples 20-23 can optionally include wherein the filter is a hygroscopic filter.

In Example 25, the subject matter of any one or more of Examples 20-24 can optionally include wherein fusing the filter and the manifold along a fused interface forms a monolithic structure.

In Example 26, the subject matter of any one or more of Examples 20-25 can optionally include wherein a fused interface is circular.

Example 27 is a method that can comprise the steps of severing a first filter from a manifold or breaking a fused interface between the first filter and the manifold, the manifold comprising: a manifold housing comprising a top surface and a sidewall extending from the top surface in a first direction, the manifold housing defining a manifold chamber, the top surface comprising an inlet port and a vacuum port disposed therein, the inlet port configured to connect to a source of medical waste fluid, the vacuum port configured to connect to a vacuum source, the manifold housing formed from a first polymer; the first filter coupled to and in communication with the vacuum port and extending away from the top surface in the first direction; washing the manifold; disinfecting the manifold; and coupling a second filter to the vacuum port to form a recycled manifold.

In Example 28, the subject matter of Example 27 can optionally include wherein each of the first filter and the second filter are hygroscopic.

In Example 29, the subject matter of any one or more of Examples 27-28 can optionally include wherein the first filter is substantially similar to the second filter.

In Example 30, the subject matter of any one or more of Examples 27-29 can optionally include wherein coupling the second filter to the vacuum port comprises mechanically fastening the second filter to a surface of the interior chamber of the manifold or a peripheral surface of the vacuum port.

In Example 31, the subject matter of Example 30 can optionally include wherein mechanically fastening the second filter further comprises press-fitting the second filter.

In Example 32, the subject matter of any one or more of Examples 27-31 can optionally include wherein coupling the second filter to the vacuum port further comprises mechanically fastening, gluing, bonding, welding, or fusing the second filter to the vacuum port.

In Example 33, the subject matter of Example 32 can optionally include wherein bonding comprises adhesive bonding.

In Example 34, the subject matter of any one or more of Examples 32-33 can optionally include wherein welding can comprise spin welding, hot plate welding, laser welding, ultrasonic welding, radio frequency welding, microwave welding, solvent welding, induction welding, and vibration welding.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for guiding medical waste fluid into a medical waste collection canister, the system comprising:

a manifold comprising a top surface and a sidewall extending from the top surface in a first direction, the top surface and the sidewall defining an interior chamber of the manifold, wherein:
  the top surface comprises an inlet port, a filter socket and a vacuum port disposed therein,
  the inlet port is configured to connect to a source of medical waste fluid,
  the vacuum port is configured to connect to a vacuum source, and
  the manifold is formed from a first polymer;
a filter positioned within the interior chamber of the manifold and immediately upstream of the vacuum port so as to filter air flowing into the vacuum port, wherein the filter comprises:
  a top filter surface positioned proximate the top surface of the manifold within the filter socket;
  a filter body connected to and extending away from the top surface of the manifold in the first direction alongside a surface of the socket; and
  a bottom filter surface connected to the filter body and positioned outside of the filter socket within the interior chamber such that the filter body directly faces the sidewall of the manifold and is exposed to the interior chamber;
wherein the filter is formed from a second polymer;
wherein the filter is fused to a surface of the interior chamber of the manifold or a peripheral surface of the vacuum port so as to form a fused interface within the filter socket, and not merely a press fit connection.

2. The system of claim 1, wherein the fused interface comprises a chemical bond between the first polymer and the second polymer.

3. The system of claim 1, wherein the fused interface is formed by melting portions of the filter and the manifold.

4. The system of claim 1, wherein the fused interface is formed by spin welding, ultrasonic welding, hot plate welding, laser welding, or radio frequency welding.

5. The system of claim 1, wherein the fused interface is formed by spin welding the filter to the manifold, spin welding comprising rapid rotation of the filter and the manifold with respect to each other, so as to melt and chemically bond the first polymer and the second polymer.

6. The system of claim 1, wherein the inlet port extends from the top surface of the manifold in the first direction a distance greater than the filter extends from the top surface of the manifold in the first direction.

7. The system of claim 1, wherein the fused interface comprises a hermetic interface.

8. The system of claim 1, wherein the first polymer or the second polymer is a thermoplastic polymer.

9. The system of claim 8, wherein the first polymer or the second polymer comprises polyethylene.

10. The system of claim 9, wherein the first polymer and the second polymer comprise polyethylene.

11. The system of claim 1, wherein the filter is a hygroscopic filter.

12. The system of claim 1, wherein the manifold and the filter are monolithic.

13. The system of claim 1, wherein a fused interface of the filter and peripheral surface of the vacuum port is circular.

14. The system of claim 1, wherein the manifold further comprises a first tab extending radially outward from a circumferential edge of the manifold.

15. The system of claim 14, wherein the manifold further comprises a second tab extending radially outward from the circumferential edge of the manifold, wherein the first tab and the second tab are spaced apart along the circumferential edge of the manifold.

16. The system of claim 15, wherein the first tab and the second tab comprise a bayonet mount.

17. The system of claim 1, wherein the inlet port further comprises a plurality of inlet ports.

18. The system of claim 1, wherein the inlet port or the vacuum port further comprises a cap removably securable thereto.

19. The system of claim 18, wherein the cap is coupled to the manifold via a tether.

20. A system for guiding medical waste fluid into a medical waste collection canister, the system comprising:
  a manifold comprising:
    a top wall having an exterior surface and an interior surface;
    a sidewall extending from the interior surface, the top wall and the sidewall defining an interior chamber of the manifold;
    an inlet port located on the exterior surface configured to fluidly connect a source of medical waste to the interior chamber;
    a filter socket located on the interior surface; and
    a vacuum port located on the exterior surface opposite the socket and configured to fluidly connect a source of medical waste fluid to the interior chamber;
  a filter positioned in the socket within the interior chamber so as to be positioned to filter air flowing into the vacuum port; and
  a fused interface between the top wall and the filter wherein the filter is fused to a surface of the interior chamber of the manifold or a peripheral surface of the vacuum port so as to form a fused interface, and not merely a press fit connection;
  wherein the manifold, the filter and the fused interface are monolithic to form a unitary structure that comprises a uniform composition throughout such that the fused interface is not different than the manifold and the filter.

21. The system of claim 20, wherein the socket comprises a flange extending away from the interior surface.

22. The system of claim 20 wherein the filter comprises:
  a bottom wall; and
  a cylindrical side body extending from the bottom wall and into the socket;
  wherein the bottom wall, the cylindrical side body and the interior surface of the top wall form a filter chamber.

23. The system of claim 20, further comprising a manifold cap releasably coupled to a free end of the sidewall.

24. The system of claim 20, wherein the filter and the socket are circular.

25. The system of claim 20, wherein the filter and the manifold are fabricated from polyethylene and the fused interface comprises inter-diffused polymer chains of polyethylene.

26. The system of claim 20, wherein the filter is a hygroscopic filter and the manifold is fabricated from a polymer.

27. The system of claim 20, wherein the inlet port includes a passage that extends through the interior chamber.

28. The system of claim 1, wherein the top filter surface abuts the top surface of the manifold such that the fused interface is proximate the top filter surface and spaced from the bottom filter surface.

29. The system of claim 1, wherein the filter is of a uniform composition throughout.

30. The system of claim 1, further comprising a spinning tool configured to receive and circumscribe the bottom filter surface of the filter to facilitate fusing of the top filter surface.

31. The system of claim 20, wherein the filter comprises:
- a top filter surface positioned proximate the top surface of the manifold within the filter socket;
- a filter body connected to and extending away from the top surface of the filter in the first direction alongside a surface of the socket; and
- a bottom filter surface connected to the filter body and positioned outside of the filter socket within the interior chamber such that the filter body directly faces the sidewall of the manifold and is exposed to the interior chamber.

* * * * *